(12) United States Patent
Karkkainen

(10) Patent No.: US 9,907,927 B2
(45) Date of Patent: Mar. 6, 2018

(54) DEVICE FOR THE CARE OF RESPIRATORY DISEASES AND FOR THE IMPROVEMENT OF PULMONARY FUNCTION

(71) Applicant: HAPELLA OY, Kiuruvesi (FI)

(72) Inventor: Aulis Karkkainen, Kiuruvesi (FI)

(73) Assignee: Happella Oy, Kiuruvesi (FI)

( * ) Notice: Subject to any disclaimer, the term of this patent is extended or adjusted under 35 U.S.C. 154(b) by 320 days.

(21) Appl. No.: 14/426,983

(22) PCT Filed: Sep. 12, 2013

(86) PCT No.: PCT/EP2013/068864
§ 371 (c)(1),
(2) Date: Mar. 9, 2015

(87) PCT Pub. No.: WO2014/041047
PCT Pub. Date: Mar. 20, 2014

(65) Prior Publication Data
US 2015/0283352 A1    Oct. 8, 2015

(30) Foreign Application Priority Data

Sep. 13, 2012 (EP) .................................... 12397523

(51) Int. Cl.
*A61M 16/16*    (2006.01)
*A61M 16/14*    (2006.01)
(Continued)

(52) U.S. Cl.
CPC ............ *A61M 16/16* (2013.01); *A61M 11/04* (2013.01); *A61M 11/044* (2014.02);
(Continued)

(58) Field of Classification Search
CPC ..... A24F 47/002; A61B 5/0813; A61K 35/14; A61M 11/00; A61M 11/002;
(Continued)

(56) References Cited

U.S. PATENT DOCUMENTS 3,757,082 A * 9/1973 Goicoechea .......... A61M 16/16
261/DIG. 65
3,855,905 A    12/1974 Carre
(Continued)

FOREIGN PATENT DOCUMENTS

CN    2 297 204 Y    11/1998
CN    2297204 Y  *  11/1998
(Continued)

OTHER PUBLICATIONS

Notification of Reason of Refusal, Japan Patent Office, Application No. 2015531551, dated Sep. 6, 2016, 8 pages.
(Continued)

*Primary Examiner* — Annette Dixon
(74) *Attorney, Agent, or Firm* — Ziegler IP Law Group, LLC

(57) ABSTRACT

A device includes a first flow channel and a liquid space for a liquid. The device also includes a second flow channel arranged in a flow connection with the liquid space, and a steam space arranged to receive steam forming in the liquid space. The first flow channel is arranged in a flow connection with the steam space. Gas flow to the device is conveyed via the second flow channel to the liquid space. Resistance is induced to the exhaled gas flow flowing through the second flow channel and pressure is increased in the liquid space. As a result of the pressure increase, steam produced in the liquid space is received in the steam space. The gas flow is conveyed from the steam space via the first flow channel to the outside of the device.

17 Claims, 4 Drawing Sheets

(51) Int. Cl.
*A61M 16/20* (2006.01)
*A63B 23/18* (2006.01)
*A63B 21/008* (2006.01)
*A61M 16/10* (2006.01)
*A61M 11/04* (2006.01)
*A61M 16/00* (2006.01)
*A61M 16/08* (2006.01)
*A61M 15/00* (2006.01)

(52) U.S. Cl.
CPC ...... *A61M 16/0057* (2013.01); *A61M 16/109* (2014.02); *A61M 16/208* (2013.01); *A63B 21/0088* (2013.01); *A63B 23/18* (2013.01); *A61M 11/042* (2014.02); *A61M 11/047* (2014.02); *A61M 15/002* (2014.02); *A61M 15/0098* (2014.02); *A61M 16/0045* (2013.01); *A61M 16/0866* (2014.02); *A61M 16/202* (2014.02); *A61M 16/209* (2014.02); *A61M 2016/0015* (2013.01); *A61M 2205/11* (2013.01); *A61M 2205/3368* (2013.01); *A61M 2205/3633* (2013.01); *A61M 2205/8206* (2013.01)

(58) Field of Classification Search
CPC .. A61M 11/003; A61M 11/005; A61M 11/02; A61M 11/04; A61M 11/042; A61M 11/06; A61M 15/00; A61M 15/0021; A61M 15/0085; A61M 15/0086; A61M 15/02; A61M 15/06; A61M 16/0045; A61M 16/0057; A61M 16/0063; A61M 16/009; A61M 16/0093; A61M 16/04; A61M 16/06; A61M 16/0666; A61M 16/0683; A61M 16/08; A61M 16/0816; A61M 16/0833; A61M 16/0875; A61M 16/104; A61M 16/1045; A61M 16/105; A61M 16/1055; A61M 16/1065; A61M 16/1085; A61M 16/109; A61M 16/12; A61M 16/125; A61M 16/127; A61M 16/14; A61M 16/142; A61M 16/16; A61M 16/162; A61M 16/18; A61M 16/20; A61M 16/201; A61M 16/206; A61M 16/208; A61M 16/22; A61M 2016/1035; A61M 2202/0085; A61M 2202/0208; A61M 2202/0225; A61M 2202/0415; A61M 2202/0427; A61M 2202/064; A61M 2205/053; A61M 2205/123; A61M 2205/505; A61M 2205/586; A61M 2205/75; A61M 2209/08; A61M 2230/437; A62B 18/045; A62B 23/02; B01F 3/0407; B05B 1/262; B05B 17/0615; B05B 7/0012; B05B 7/0483; G01N 21/714; H01L 21/67017; H01L 21/67766; Y10S 128/909; Y10S 128/91; Y10S 128/911; Y10S 261/65; Y10S 55/35; Y10T 137/4891; Y10T 137/87603; Y10T 137/87627
USPC ............ 128/200.14, 200.16, 200.18, 200.21, 128/200.22, 200.2, 201.13, 201.24, 128/201.25, 203.12, 203.15, 203.16, 128/203.17, 203.26, 203.27, 203.28, 128/204.16, 204.17, 204.18, 204.24, 128/204.25, 205.11, 205.12, 205.17, 128/205.24, 205.29, 207.14, 909, 910, 128/911
See application file for complete search history.

(56) References Cited

U.S. PATENT DOCUMENTS

| | | | | |
|---|---|---|---|---|
| 4,028,526 A | * | 6/1977 | Schossow | H02H 11/001 128/203.27 |
| 4,036,919 A | * | 7/1977 | Komendowski | A61M 16/16 128/200.13 |
| 4,054,622 A | | 10/1977 | Lester | |
| 4,621,641 A | * | 11/1986 | Frank | A61H 33/12 392/404 |
| 5,461,695 A | * | 10/1995 | Knoch | A61M 11/06 392/394 |
| 5,603,314 A | * | 2/1997 | Bono | A61M 11/06 128/200.14 |

FOREIGN PATENT DOCUMENTS

| | | |
|---|---|---|
| CN | 102046232 A | 5/2011 |
| CN | 202427014 U | 9/2012 |
| EP | 0 513 712 A1 | 11/1992 |
| GB | 1 332 382 A | 10/1973 |
| JP | S4949076 A | 5/1974 |
| JP | 2002035163 A | 2/2002 |
| RU | 1790417 A3 | 1/1993 |
| WO | 02/092157 A1 | 11/2002 |

OTHER PUBLICATIONS

Federal Service for Intellectual Property, "The Federal Institute of Industrial Property", Application No. 20151104711/14(016454), dated Nov. 10, 2016, 11 pages.

Office Action, China Patent Office, Application No. 201380047552.1, dated Jan. 26, 2016, 9 pages.

* cited by examiner

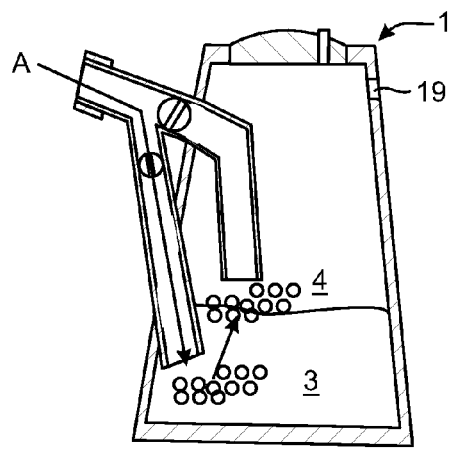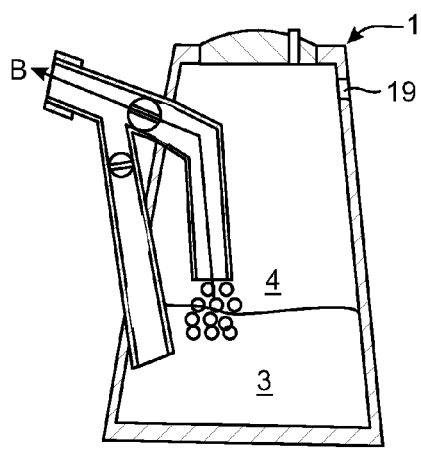
Fig. 3a   Fig. 3b
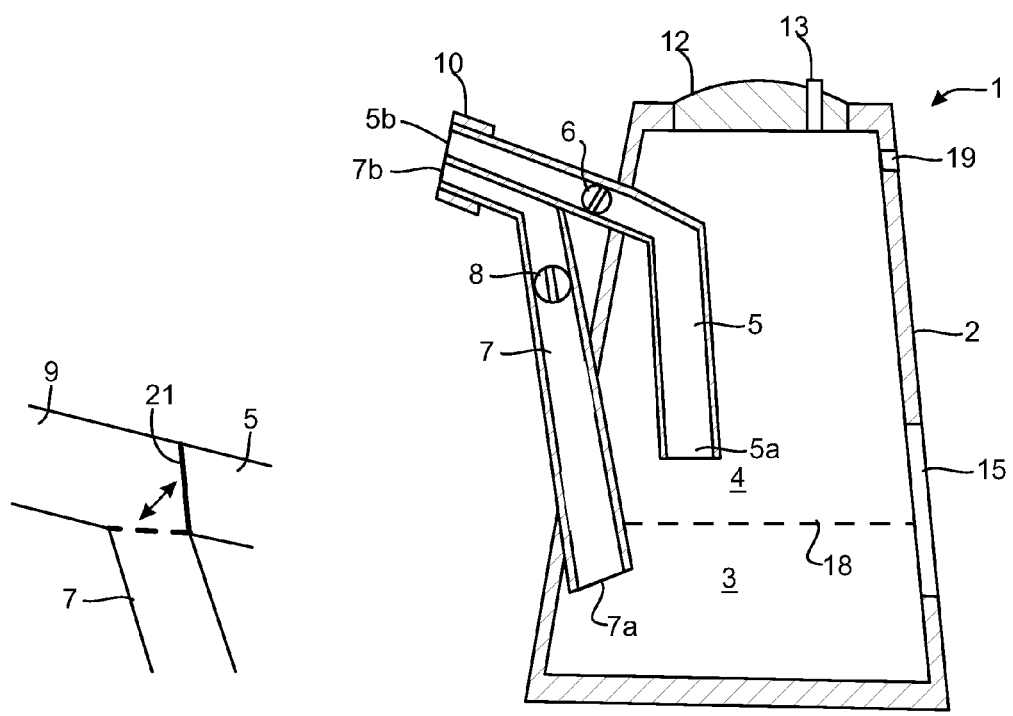
Fig. 4   Fig. 5

DEVICE FOR THE CARE OF RESPIRATORY DISEASES AND FOR THE IMPROVEMENT OF PULMONARY FUNCTION

FIELD

The disclosed embodiments relate to a device for the care of respiratory diseases and/or for the improvement of pulmonary function, comprising at least a first flow channel for inhalation, a body part, and a liquid space in the body part for liquid. Furthermore, the disclosed embodiments relate to a method for guiding gas flows in a device comprising at least a first flow channel for inhalation, a body part, and a liquid space in the body part for liquid.

BACKGROUND

The incidence of various allergies and respiratory tract infections has strongly increased recently. This may easily have the result that a patient with a respiratory disease is subjected to continuous pharmacotherapy and repeated antibiotic regimes. These may have adverse effects and cause new problems. Mucus excreted in bronchitis and infection factors easily remain in obstructed small bronchial tubes and pulmonary alveoli, causing shortness of breath. Therefore, in practice, it is often difficult for inhaled drugs to have a strong effect on those areas of the respiratory organs where the actual therapy would be needed.

In obstructive pulmonary diseases, such as asthma and chronic obstructive pulmonary disease, the obstruction of the airways restricts the flow of air in strong exhalation. In asthma, the bronchial tubes are obstructed as a result of an inflammation, and in chronic obstructive pulmonary disease, the symptoms are caused by a long-lasting inflammation and obstruction of the pulmonary alveoli and by the stiffening of the thorax resulting from these. In obstructive pulmonary diseases, the symptoms include shortness of breath and mucus in the airways. Furthermore, the symptoms can be aggravated by thoracic muscle tension resulting from the diseases. Moreover, in acute respiratory tract infections, the bronchial tubes of the patients may easily become irritated and inflamed. In respiratory tract infections, coughing removes mucus and makes it rise higher from the bronchial tubes. In a patient with asthmatic symptoms, a respiratory tract infection contracts the bronchial tubes and thereby causes shortness of breath, and mucus cannot be sufficiently removed by coughing, wherein the mucus accumulates in the respiratory tract and increases the risk of catching e.g. pneumonia.

In the care of pulmonary diseases and respiratory tract infections, blowing into a bottle and steam inhalation have been used as non-pharmacological remedies at home. When blowing into a bottle, the patient blows through a hose into a bottle that contains water. Such resisted blowing removes mucus and opens bronchial tubes. Steam inhalation, in turn, moistens the bronchial tubes and makes the excreted mucus more fluid.

Pulmonary diseases increase cardiac loading and aggravate heart-related diseases, such as the occurrence of arrhythmias (for example, atrial fibrillation).

In the care of respiratory diseases and allergies, various inhalators and steam inhalers have been used for conveying water vapour to the lungs by inhalation. However, such devices and methods may involve the drawback that the temperature of the water vapour to be inhaled is too high, which may damage the respiratory organs and cause a risk of burn. Furthermore, if the aim is to use the water vapour for carrying a drug to the lungs, only part of this drug will end up in the lungs, because most of the water vapour is not inhaled but evaporated in the ambient air.

The publication WO 02/092157 discloses a portable medical gas humidifier, which may be used with portable sources of contained oxygen or other breathable gases. The device consists of a reservoir for water and connections from the source of breathable air (or gas) and to the patient's breathing device. When connected, all of the breathable air source (or gas) passes quietly through the reservoir and becomes "humidified". The device is intended to humidify the air which a patient inhales. The humidifying is achieved by providing pressurized oxygen from the top of the device inside the reservoir containing water, wherein the oxygen is forced to the bottom of the reservoir and produces bubbles to moisturize the oxygen which the patient inhales. The pressure of the oxygen makes it easier for the patient to inhale i.e. the inhalation resistance is reduced when this device is used, wherein the pulmonary alveoli of the patient are not efficiently opened.

The publication CN 2297204Y discloses a breathing recovery exercising apparatus, which is composed of a container and a breathing tube which is communicated with the container. A baffle is arranged in the container and divides the container into an inhalation air chamber and an exhalation air chamber which are respectively provided with a pressure regulating air inlet tube and a pressure regulating air inlet tube. The breathing tube is formed into an inverted Y shape by an inhaling tube and an exhaling tube, in which non-return flaps are respectively arranged. The breathing recovery exercising apparatus has an exercising means with three functions of inhalation, exhalation, and combined inhalation and exhalation. The pressure in the inhalation air chamber is generated by an external pressure source. Therefore, the device cannot utilize the pressure of the exhalation air in the operation of the device. Furthermore, the positive effect that pulmonary alveoli of the user are opened more efficiently which strengthens the lungs and also improves the efficiency of inhalation is not achieved by the device of CN 2297204Y.

The publication GB1332382 discloses a device which may be adjusted to function as either a humidifier or an atomizer. The device comprises a chamber, a valve housing, an upper conduit and a lower conduit each of which communicates with a cavity formed in the valve housing. The lower conduit is also communicating with the chamber. The device also comprises a valve spool received in the cavity to define with the housing a valve chamber. When the device is used as a humidifier the valve spool is positioned to align passageways with the upper and lower conduits to allow air or oxygen to pass from the upper conduit to the lower conduit through the water in the chamber, and to a patient through a gas outlet tube. When the device is used as an atomizer a passageway of the valve spool is aligned with the upper conduit so that gas can pass from the upper conduit to the valve chamber through an orifice, and water can pass from the lower conduit to the valve chamber through a groove, the velocity of the gas through the orifice creating a vacuum in the valve chamber which draws the water into the chamber, and causing the water to break up into droplets to form an aerosol, which passes through the orifice and outlet tube to a patient. The device of GB1332382 may only be used during inhalation stage.

SUMMARY

It is an aim of the disclosed embodiments to reduce the above-mentioned drawbacks and to provide an improved device for the care of respiratory diseases. The invention utilizes exhalation with resistance and steam inhalation combined with it, integrated in a single functional process where the different steps support each other. Blowing with resistance is effective in opening particularly the small bronchial tubes in the lower part of the lungs and activates the muscles that run between the ribs by increasing the volume of the airways. As a result, in the inhalation step, moist steam can better reach the small bronchial tubes, and at the same time it makes the mucus more fluid and more easily removable. The invention is thus based on the idea that the device is used in both exhalation and inhalation in such a way that before the inhalation step, the device is used to provide a flow resistance for the exhalation; as a result, it is possible e.g. to open pulmonary alveoli and in this way to enhance the access to the pulmonary alveoli by moist steam flowing into the lungs in the inhalation step. Thus, the effect of a drug or another active agent possibly carried by the moist steam can be boosted in the lungs. To put it more precisely, the device according to the present invention is primarily characterized in that the device further comprises:

a second flow channel arranged in a flow connection with the body part;

a steam space arranged to receive steam forming in the liquid space, whereby the first flow channel is arranged in a flow connection with the steam space;

means for conveying an exhaled gas flow from the outside of the device via the second flow channel to the body part;

means for inducing resistance to the exhaled gas flow flowing through the second flow channel; and means for conveying a gas flow from the steam space via the first flow channel to the outside of the device during inhalation.

The method according to the disclosed embodiments is primarily characterized in that the device also comprises a second flow channel which is arranged in a flow connection with the body part, and a steam space, wherein in the method:

a gas flow to the device is conveyed via the second flow channel to the body part;

inducing resistance to the exhaled gas flow flowing through the second flow channel;

increasing the pressure in the liquid space, as a result of the pressure increase, steam produced in the liquid space is received in the steam space, the gas flow is conveyed from the steam space via the first flow channel to the outside of the device.

By the device and the method disclosed, it is possible to enhance and facilitate the care of particularly respiratory diseases and to intensify the function of the lungs. By applying the device and the method according to the invention, it is possible to reduce or even avoid the use of cortisone and other products to open up the lungs. Furthermore, the efficiency of inhalable pulmonary drugs can be improved by the device according to the invention. The efficiency of inhalable pulmonary drugs presently in use is about 40 to 60%.

In normal inhalation, the diaphragm and the outer costal muscles are contracted, and in relaxed exhalation, the respiratory muscles are relaxed and air comes out as the muscles return from a stretched state to a resting state. In strong exhalation, the abdominals and the innermost intercostal muscles are used. Thus, the small bronchial tubes and terminal units are contracted more strongly in the lower parts of the lungs than in the upper parts of the lungs.

The device can be utilized, inter alia, in improving the pulmonary function of aging patients and children. With age, the thorax becomes stiffer and breathing is more superficial, predisposing to pneumonias. Children with asthmatic symptoms limit their movements in exercise and get used to more superficial breathing. Thus, the capacity of the lungs is reduced.

The disclosed device can utilize the patient's own respiratory mechanism, inter alia, by directing the desired resistance on the lungs during exhalation and inhalation, wherein even the smaller bronchial tubes are forced to work; as a result, accumulated mucus etc. can start to move out of the bronchial tubes more efficiently than when solutions of prior art are used.

In an advantageous embodiment of the disclosure, during exhalation the air is introduced into a water/drug mixture which is bubbled up by pressure and is vaporized into the air space of the device. During inhalation, a separate valve closes the liquid channel and opens the air space, into which a desired amount of replacement air is introduced, if necessary, via a valve above the air space. The replacement air passes via the steam/drug in the air space of the device to the lower part of the air space, and is simultaneously mixed with the steam mixture. In the inhalation step, some of the vapourized oxygen/drug mixture formed in the air space is drawn into the lungs and introduced during the inhalation into the lungs and also into the most severely inflamed areas where the small bronchial tubes become free from mucus and are opened. The steam to be inhaled into the lungs moistens and dissolves mucus, making it more fluid and more easily removable.

Each repetition can contribute to the effect of the operation, and in some cases even after about 5 to 10 repetitions most of the drug has risen from the liquid to the steam space and been introduced into the lungs.

The patient using the device blows e.g. into the liquid or via a choke, against the resistance, in the same way as in exhalation, wherein the pressure in the bronchial tubes increases as the abdominals and the intercostal muscles are contracted and the small bronchial tubes and the alveoli in the lower part of the lungs are contracted most. This may contribute to the removal of mucus from the lower part of the lungs, and particularly the risk of pneumonia can be reduced. Furthermore, by means of the device, the patient can inhale warm steam, to which it is possible to add salt or a drug for treating the bronchial tubes. Salty water vapour acts in the same way as physiological saline (0.9% NaCl) which flushes out irritated bronchial tubes and moistens the mucus excreted, making it more fluid and more easily removable. The device can enhance the non-pharmacological care of a respiratory tract infection at home and reduce the risk of pneumonia, particularly in patients with asthmatic symptoms. Furthermore, exhalation with resistance activates and strengthens the abdominals and intercostal muscles involved in respiration, and may improve the elasticity of the thorax as well as the breathing. Particularly in obstructive lung diseases, such as asthma and chronic obstructive pulmonary disease, the intercostal muscles are strongly contracted, and partly therefore the thorax becomes stiffer. Furthermore, the steam to be inhaled may enhance the effect of the device to flush out the airways and to remove mucus, particularly in connection with infections.

BRIEF DESCRIPTION OF THE DRAWINGS

In the following, the aspects of the disclosed embodiments will be described in more detail with reference to the appended drawings, in which FIGS. 3a and 3b show the function of flow channels in different breathing steps in principle views, FIG. 4 shows an alternative valve arrangement for guiding air flows in the different functional steps of the device, FIG. 5 shows an alternative arrangement of flow channels in the device.

DETAILED DESCRIPTION OF THE DISCLOSED EMBODIMENTS

Figure 1:
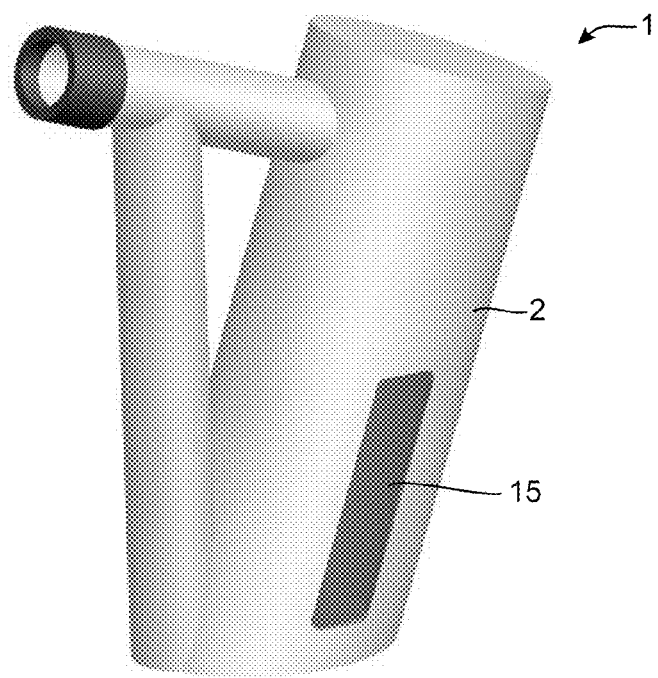
FIG. 1 shows a device according to an embodiment in a perspective view.
Figure 2:
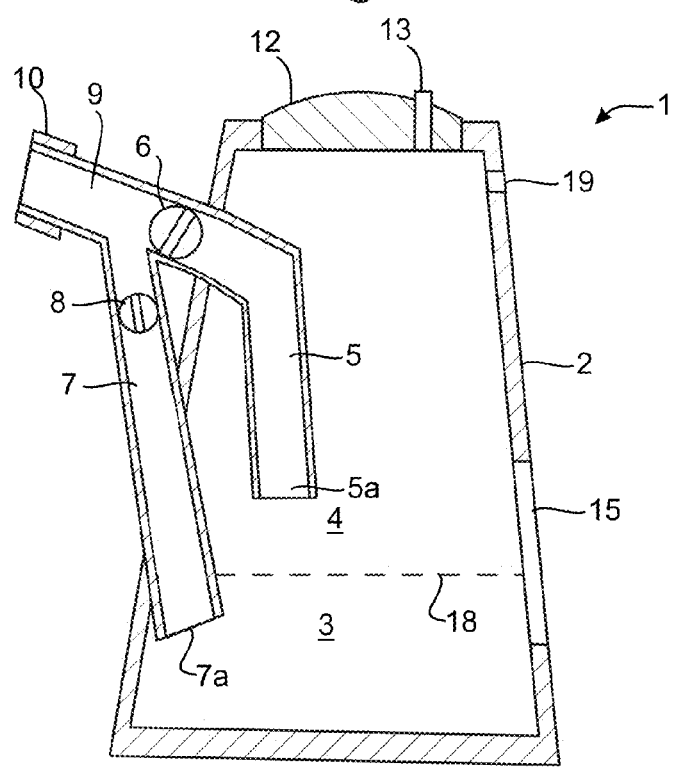
FIG. 2 shows a device according to the embodiment of FIG. 1 in a reduced cross-sectional view.

FIG. 1 shows a perspective view of a device 1 according to an advantageous embodiment of the disclosure, and FIG. 2 shows the device of FIG. 1 in a reduced cross-sectional view. The device 1 comprises a body part 2 whose inner volume is provided with a liquid space 3 for a liquid, such as water. The body part 2 is advantageously thermally insulated either in part or in whole, to reduce heat losses. Above the liquid space 3 there is a steam space 4, to which the steam rising from the liquid can be transferred. The device 1 also has a first flow channel 5 which can be used at least in the inhalation step, for conveying an air flow to the mouth and further to the lungs of the person to be cared for. In connection with the first flow channel 5 a first valve 6 is provided, by means of which the air flow in the first flow channel 5 can be adjusted or prevented substantially totally, if needed, as will be described further below in this description. The first flow channel 5 extends to the steam space 4 in such a way that one end 5a of the first flow channel 5 is above the liquid level even at the stage when the liquid space 3 is filled with liquid. The liquid level in a situation is illustrated with a broken line 18, but it is obvious that the liquid level can vary in different situations.

Although in this context the liquid space 3 and the steam space 4 are mentioned separately, they are not necessarily separated from each other structurally but these spaces are formed in the inner volume of the body part 2, wherein the term 'liquid space' can be used for that part of the inner volume which is filled with liquid at a time, and correspondingly, the term 'steam space' can be used for that part of the inner volume to which steam can be transferred from the liquid.

At the liquid space 3, the wall of the body part 2 can comprise a transparent section 15 (a window), through which the liquid level in the liquid space 3 can be seen. This may, among other things, facilitate the filling of the liquid space 3, so that it can be seen from the outside of the device 1, when the liquid space 3 is filled with a suitable quantity of liquid.

The device 1 can also be provided with a lid part 12, through which liquid, such as water, can be supplied into the liquid space 3. The lid part 12 can be fastened relatively tightly to the body part 2 so that a sufficient pressure level can be maintained inside the body part during the use of the device 1.

The body part 2 or the lid part 12 is preferably provided with a replacement air valve 19, through which replacement air can be supplied into the inner volume of the body part at the inhalation step.

The device 1 has also a second flow channel 7 for conveying air to be blown out into the device 1. In connection with the second flow channel 7, a second valve 8 is provided, by means of which the air flow in the second flow channel 7 can be adjusted or prevented substantially totally, if needed, as will be described further below in this description. This second flow channel 7 extends to the liquid space 3 in such a way that one end 7a of the second flow channel 7 is below the surface of the liquid when the liquid space 3 is filled with liquid. In this embodiment, the first flow channel 5 and the second flow channel 7 are connected to a third flow channel 9. This third flow channel 9 can constitute a mouthpiece 10 for the device 1, or the device 1 may comprise a separate mouthpiece 10, through which the third flow channel 9 is led.

In some cases, the mouthpiece 10 can be replaceable, wherein persons using the device can each have their own mouthpiece 10.

In some embodiments, the second flow channel 7 of the device 1 is provided with an adjustable flow resistance, such as a throttle, by means of which the resistance on the exhalation can be adjusted as needed. On the other hand, in some situations the flow resistance can be adjusted by changing the viscosity of the liquid in the liquid space 3.

In some embodiments, the first flow channel 5 of the device 1 can also be provided with an adjustable flow resistance, such as a throttle, by means of which the resistance on the inhalation can be adjusted as needed. On the other hand, the flow resistance of the first flow channel 5 may, as such, be sufficiently high to provide a suitable resistance in the inhalation step. In some cases, this flow resistance can be suitably set by, for example, selecting the cross-sectional area of the flow channel in a suitable way. If the first flow channel 5 and/or the second flow channel 7 or a part of them is made of a tube, such as a plastic or metal tube, the flow channel can be set, for example, by selecting the diameter of the tube in a suitable way or by placing a tube with a smaller diameter at some location in the first flow channel 5 and/or the second flow channel 7.

In the following, the operation of the device according to FIG. 1 will be described in a care situation with reference to FIGS. 3a and 3b. The liquid space 3 of the device is filled with a liquid, such as water, to a given height level. This height level is advantageously such that one end 5a of the first flow channel 5 is above the liquid level, but one end 7a of the second flow channel 7 is below the surface of the liquid. This one end 7a of the second flow channel 7 forms a kind of an opening which connects the second flow channel 7 to the liquid space 3, wherein the gas flow flowing through the second flow channel 7 is arranged to be directed to the liquid space 3 in order to increase pressure in the liquid space 3. The liquid to be supplied to the liquid space is preferably heated, for example by a separate heating device, or warm water is supplied into the liquid space from the hot water tap of a building, or the like. The target temperature of the liquid may vary in different situations, but it has been found that in the care of respiratory diseases, the temperature of the liquid should not be boiling but, for example, 60 to 70 degrees at the most, or even cooler. Thus, if the temperature of the liquid rises higher than the target temperature at the heating stage, there may be a need to allow the liquid to cool down before the device 1 is used by the person to be cared for.

When the liquid space 3 has been filled with a suitable quantity of the liquid and the temperature of the liquid is suitable, the care measures can be started. The person to be cared for places the mouthpiece 10 in his/her mouth and starts to blow. Thus, the air from the subject's lungs flows into the third flow channel 9 and from there further to the second flow channel 7. In practice, air can flow into the first flow channel 5 as well, but the first valve 6 in the first flow channel is in a position that prevents the air from flowing further in the first flow channel 5. In other words, the first valve 6 prevents the air from flowing via the first flow channel 5 into the steam space 4. Instead, the second valve 8 in the second flow channel 7 is in a position that allows the exhaled air to flow into the liquid space 3. The liquid in this liquid space 3 causes a flow resistance which has the effect that the person has to blow harder so that the exhaled air can flow into the liquid space 3. This has been found to be useful in the care, because the muscles involved in the function of the lungs have to work harder, which also strengthens these muscles when the care is continued. Furthermore, the opening of the bronchial tubes is more effective, when a clearly resisting force effect is produced against the exhalation. The air flows of this step are illustrated with an arrow A in FIG. 3a.

In the liquid space 3, the exhalation has the effect that bubbles (pores) are formed in the liquid and the pressure inside the body part, e.g. in the liquid space 3, increases. As a result, part of the liquid in the liquid space 3 is evaporated and this steam rises to the steam space 4, although the temperature of the liquid is below the evaporating point of the liquid. If the liquid space 3 or the steam space 4 contains a drug, the delivery of the drug with the inhaled steam into the lungs is enhanced as well. The exhalation is followed by an inhalation step which induces the following chain of operations in the device 1. When the person starts to inhale by drawing air through the mouthpiece 10 into his/her lungs, an underpressure is formed in both the first flow channel 5 and the second flow channel 7. Thus, the second valve in the second flow channel 7 is closed and prevents the flow of air through the second flow channel 7 into the lungs. Instead, the first valve 6 in the first flow channel 5 opens and lets air flow from the steam space 4 through the first flow channel 5 into the lungs. This inhaled air also entrains steam from the steam space 4; in other words, the device functions as a steam inhaler. The air flows of this step are illustrated with an arrow B in FIG. 3b. Because the inhalation step follows the exhalation step substantially immediately, the bronchial tubes do not have time to close, which is substantially effective and enhances the access to the lungs by steam and possible drugs contained in it. Both the blowing resistance and the inhalation resistance can be adjusted, because the lungs and the muscles supporting them are activated in the resisted inhalation as well.

In the above described step 1, the first valve 6 and the second valve 8 are automatically pressure-operated valves, kind of back-pressure valves, by which the guidance of the air flow can be operated in a controlled manner as desired. In the device 1 according to the invention, it is also possible to use other kinds of valves, by which the control of the air flow can be implemented by applying the above-mentioned principle. As an example, manually operated valves can be mentioned. The user him/herself or his/her assistant can adjust the valves according to the need; consequently, in the exhalation step, the flow through the first flow channel 5 is prevented, and in a corresponding manner in the inhalation step, the air flow through the second flow channel 7 is prevented. In an embodiment, the first valve 6 and the second valve 8 can be replaced by a single valve with a shutter (for example baffle 21, FIG. 4) which can alternately close the first flow channel 5 and the second flow channel 7. The control of the valves 6, 8 can also be implemented by automation, wherein a sensor or the like may be needed to detect if the person is breathing out or in and, on the basis of this, to control the operation of the valves 6, 8 in an appropriate way.

In the device 1 of FIG. 1, the first flow channel 5 and the second flow channel 7 are connected at one end 5b, 7b to a single flow channel, that is, the third flow channel 9. However, the device 1 according to the invention can also be implemented in such a way that the third flow channel 9 is not needed but both the first flow channel 5 and the second flow channel 7 are led to the mouthpiece 10, whereby both the second end 5b of the first flow channel 5 and the second end 7b of the second flow channel 7 are in the mouthpiece and the person places these in his/her mouth for the time of using the device. Said second end 5b of the first flow channel 5 and the second end 7b of the second flow channel 7 are close to each other, advantageously in parallel, on top of or obliquely to each other in such a way that the second ends 5b, 7b of both flow channels fit in the subject's mouth simultaneously. One example of such an implementation is shown in FIG. 5.

Figure 6:
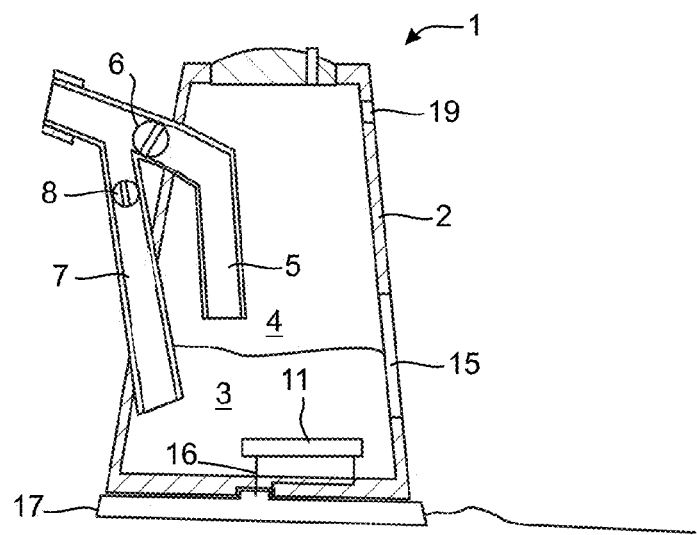
FIG. 6 shows a device according to another embodiment in a reduced cross-sectional view.

In connection with the operation of the above-described device 1, it was mentioned that the liquid is heated outside the device 1, for example by a separate heater, such as a coffee maker, a kettle, or the like. The invention can also be applied in such a way that the heating of the liquid is arranged in the device 1 itself, or the device 1 can be heated from the outside for heating the liquid in the liquid space 3 of the device. FIG. 6 shows a reduced cross-sectional view of a device 1 according to another embodiment, comprising liquid heating means 11 for heating the liquid. Thus, the heating of the liquid in the liquid space 3 can be performed by liquid heating means 11. The liquid heating means 11 can be implemented, for example, by means of a heating resistor, wherein electricity is conducted to the heating resistor for the time of heating. The electric energy needed for the heating can be conducted, for example, by electric energy transmission means 16 provided in the bottom 2a of the body part, or the device can be provided with a stationary electric wire which is connected e.g. to an electrical outlet or converter when heating is needed. If said electrical energy transmission means are provided at the bottom 2a of the device, the device 1 can be provided with a base 17 with corresponding means which can be connected either directly or inductively to the electric energy transmission means of the device. For a person skilled in the art, it is obvious how such electric energy transmission can be implemented in a wired or wireless manner, so a more detailed description of it in this context will not be necessary.

Advantageously, the device 1 also comprises a lid part 12 which can be opened and/or removed, for example for filling the liquid space 3. The lid part 12 or the body part 2 can also be provided with a relief valve 13 which may prevent the pressure from rising too much inside the device 1. The lid part 12 can also be provided with an opening, through which a drug or another substance can be supplied to the liquid in the liquid space. On the other hand, the inner volume of the device 1, for example the inner surface of the body part, can be provided with a container or the like, to which the drug can be supplied and from which the drug is gradually transferred to the liquid in the liquid space 3.

If the device 1 is provided with liquid heating means 11 of the above-mentioned type, it may also be necessary to provide the device 1 with control means (not shown in the appended drawings) for controlling the heating process, inter alia to avoid excessive heating. With the control means it is possible, for example, to control the temperature of the liquid, wherein it is possible to use liquids at different temperatures for different uses.

In an advantageous embodiment, the liquid heating means 11 can also be used, among other things, for disinfecting the device. Thus, the liquid is heated to a higher temperature than in a care situation, for example to the boiling point (100 degrees). This will clean at least part of the impurities, wherein the use of the device 1 in care situations may be safer. During the disinfecting step, the use of the device for care is preferably prevented. This can be implemented, for example, in such a way that the first valve 6 and the second valve 8 are placed in a position which prevents the flow of air from the liquid space 3 and the steam space 4 to the mouthpiece 10.

The device 1 can also be washed with a dishwashing liquid either by hand or in a dishwasher, or ultrasonic cleaning or the like can be used.

In the following, we will briefly present some further heating methods. Applying them in practice may require that the requirements of the different heating methods are taken into account in the structure of the device 1, including for example the heat resistance. One possible heating method is to place the device on a heating element (for example, a hot plate of an electric stove), wherein the heat of the heating element is conducted through the bottom of the body part to the liquid in the liquid space 3. A heating method of a corresponding type is to use a campfire for heating the liquid. Yet another possibility may be to use a microwave oven, wherein the device 1 is placed in the microwave oven. Thus, the device 1 should not contain such materials which could hamper the operation of the microwave oven and which are hardly heated by microwaves at all. Some kinds of heating methods based on thermochemical phenomena may also be used. In this context, one should mention so-called heat cartridges which can be placed on the bottom of the device for heating. The heat cartridges can be based on using, for example, sodium acetate, iron dust, burnt lime, or aluminium chloride.

In some cases, the heating means of the device 1 can be driven by, for example, a battery, whereby the device can also be used in situations in which there is no separate source of electrical energy available.

The device 1 can also be provided with other automation and control for e.g. informing the user of the device about a possible need for maintenance, displaying the temperature of the liquid, etc.

In an advantageous embodiment, the device 1 is used for storing treatment sessions in a memory, so that it is possible to monitor the outcome of the treatments and to follow up on progress in the care. This may be useful, for example, for nursing staff who may use the data to make sure that the care has been taken in due course and appropriately.

Figure 7:
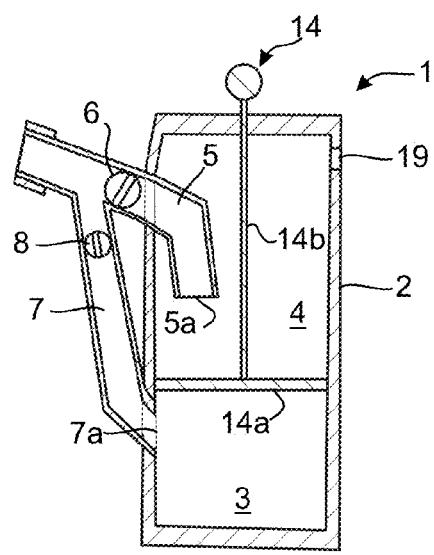
FIG. 7 shows a device according to yet a third embodiment in a reduced cross-section.

FIG. 7 shows a reduced cross-sectional view of yet another advantageous embodiment of the device 1. It comprises pressurizing means 14 for increasing the pressure prevailing in the liquid space 3. This may be needed, for example, in situations in which the person to be cared for is not capable of blowing air sufficiently strongly into the device 1 during exhalation. The pressurizing means 14 comprise, for example, a piston 14a or the like which can move in the inner volume of the body part, for example towards the bottom part 2a and away from the bottom part 2a. This movement can be produced, for example, by pressing the rod 14b downwards or by lifting the rod 14b upwards. Because the pressure increase preferably has to be produced in the liquid in the liquid space 3, and steam forming in the liquid should still enter the steam space 4, the piston 14a is advantageously equipped with channels or the like, through which steam can rise to the steam space 4. Although the piston 14a is thus not fully sealed, the piston 14a can still be used for increasing the pressure in the liquid space 3. Such pressurizing means 14 can be employed by, for example, the user of the device or his/her aide. The required pressure level can be set according to the user's feelings, wherein it is possible to avoid applying too high a pressure.

Figure 8:
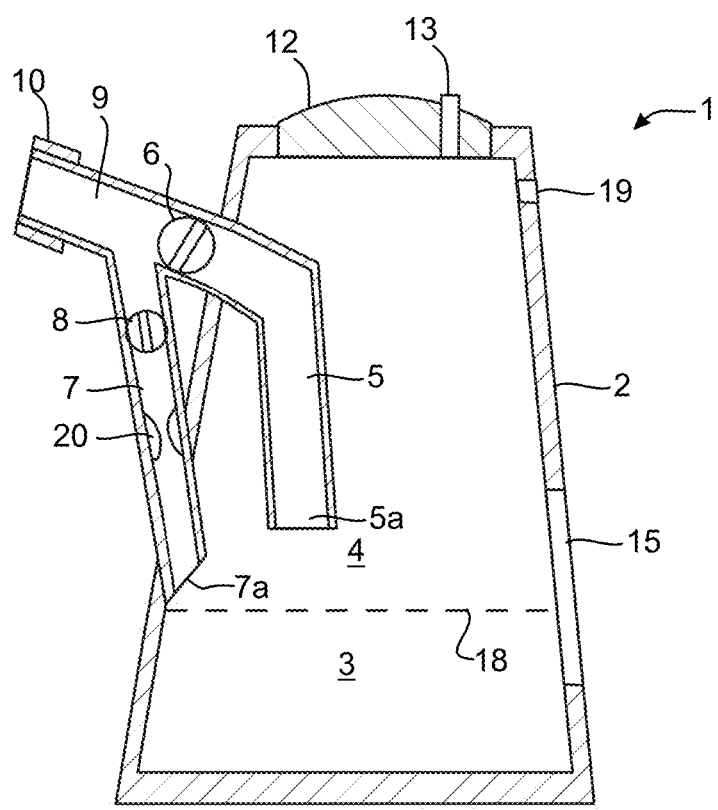
FIG. 8 shows a device according to yet a fourth embodiment in a reduced cross-section.

FIG. 8 shows a reduced cross-sectional view of yet another advantageous embodiment of the device 1. In this embodiment the second flow channel 7 is provided with a choke 20 or similar which may induce or increase flow resistance affecting to the gas flow in the second flow channel 7. Hence, this may increase the exhalation resistance which a person using the device encompasses. This kind of blowing with resistance may increase the efficiency of the functioning of lungs, as was already explained above. In this embodiment the exhaled air is not necessarily conducted from the second air channel 7 directly to the liquid space 3, but to the steam space 4 above the liquid space 3. The other parts of the device 1 may correspond with some of the earlier described embodiments.

It is also possible to combine the fourth embodiment and some of the other embodiments. In other words, the choke 20 may also be used in the device 1 in which one end 7a of the second flow channel 7 is in the liquid space 3.

In some embodiments, an external pressure source can be used, such as a compressor (not shown) for increasing the pressure in the liquid space 3.

The device 1 can be used in a variety of situations to help the subject's respiratory organs in their function. The device 1 is suitable for the care of, for example, asthma, allergies of the respiratory tract, chronic obstructive lung disease, as well as other pulmonary diseases, infections of the upper respiratory tract (cold), etc. By means of the device 1 according to the invention, it is also possible for athletes to improve their performance, for example by strengthening their respiratory muscles and improving the function of their lungs, as well as by removing harmful mucus and opening the airways.

In some cases, the device 1 can also be applied for the care of animals. This may require some modifications in the structure of the device, while the principle of operation remains the same.

The use of the device 1 is not limited solely to the care of diseases, but the device 1 can also be used for improving the function of the respiratory organs of e.g. singers, voice users, etc. Because the device is suitable for use by persons of all ages as a form of care of e.g. cough and/or cold and, among other things, it may simultaneously strengthen the breathing mechanism, the device is suitable for use during a person's whole life span.

Although the disclosed embodiments were described above by using the application of a warm liquid as an example in the care session, it is also possible to use a cold liquid in connection with the device 1. In some treatments or corresponding situations, it may be advantageous to use a cold liquid, even a liquid whose temperature is below 0 degrees. In such a situation, cold steam may rise from the liquid space, being conveyed to the subject's lungs during the inhalation step.

Furthermore, it should be noted that air was used as an example of the gas flow in the description above, but it is obvious that in addition to air, the gas flow to be conveyed into and from the device may also comprise other substances than air, such as components evaporated from drugs.

The present invention is not limited to the above-presented embodiments, but it can be modified within the scope of the appended claims.

The invention claimed is:

1. A device comprising
   at least a first flow channel for inhalation;
   a body part having an inner volume comprising a first part and a second part above the first part, wherein the first part is configured to receive liquid to partly fill the first part;
   a mouthpiece for providing gas flow from the first flow channel to a user of the device during inhalation and for receiving exhaled gas flow from the user;
   a second flow channel arranged in a flow connection with the first part of the inner volume and adapted to provide exhaled gas into the liquid;
   wherein the second part of the inner volume is arranged to receive vaporized liquid from the first part, whereby the first flow channel is arranged in a flow connection with the second part;
   a first gas flow conveying element for conveying a gas flow from the second part via the first flow channel to the outside of the device during inhalation;
   a second gas flow conveying element for conveying an exhaled gas flow from the outside of the device via the second flow channel to the first part of the inner volume to increase pressure in the inner volume; and
   a flow resistance increasing element for inducing resistance to the exhaled gas flow flowing through the second flow channel;
   a relief valve to prevent pressure from rising too high inside the device during exhalation; and
   a replacement air valve to introduce replacement air into the second part during inhalation;
   wherein the first gas flow conveying element comprises a first valve for preventing gas flow through the first flow channel into the second art during exhalation and for enabling gas flow through the first flow channel from the second part during inhalation; and
   wherein the second gas flow conveying element comprises a second valve for preventing gas flow through the second flow channel from the first part during inhalation and for enabling gas flow through the second flow channel into the first part during exhalation.

2. The device according to claim 1, wherein the flow resistance increasing element comprises an opening, which connects the second flow channel to the first part, wherein gas flow from the second flow channel is arranged to be conducted to the first part for increasing the pressure in the first part.

3. The device according to claim 1, wherein the flow resistance increasing element comprises a choke.

4. The device according to claim 1, wherein the first valve is a valve that is closed by underpressure.

5. The device according to claim 1, wherein the device also comprises a heater for heating the liquid in the first part.

6. The device according to claim 5, wherein the heater is adapted to disinfect the device.

7. The device according to claim 6, wherein the first gas flow conveying element and the second gas flow conveying element are configured to prevent gas flow' from the first part and the second part to the mouthpiece during disinfection of the device.

8. The device according to claim 1, wherein the device also comprises a third flow channel, to which the first flow channel and the second flow channel are connected in such a way that conveying the gas flow from the outside of the device to the second flow channel and conveying the gas flow from the first flow channel to the outside of the device are arranged via the third flow channel.

9. The device according to claim 1, wherein the device also comprises a pressurizer for increasing the pressure in the first part.

10. The device according to claim 1, wherein the device is intended to be used in the care of respiratory diseases.

11. The device according to claim 1, wherein at least one of the first flow channel and the second flow channel comprises an adjustable flow resistance.

12. Use of the device of claim 1 for resistive exhalation and inhalation.

13. A method for using a device comprising at least a first flow channel for inhalation, a body part having an inner volume comprising a first part and a second part above the first part, and a second flow channel arranged in a flow connection with the body part, the method comprising:
   receiving liquid to partly fill the first part of the inner volume;
   providing, via a mouthpiece, a gas flow from the first flow channel to a user of the device during inhalation;
   receiving exhaled gas flow from the user via the mouthpiece;
   conveying, by a second gas flow conveying element, the received exhaled gas flow to the device via the second flow channel to the body part,
   inducing resistance, by a flow resistance increasing element, to the exhaled gas flow flowing through the second flow channel;
   increasing pressure in the first part;
   receiving, in the second part of the inner volume, vaporized liquid produced in the first part as a result of the pressure increase,
   using a relief valve to prevent pressure from rising too high inside the device during exhalation;
   using a replacement air valve to introduce replacement air into the second part during inhalation;
   conveying by a first gas flow conveying element gas flow from the second part via the first flow channel to outside of the device,
   wherein the method further comprises
      using a first valve in the first gas flow conveying element to:
         prevent gas flow through the first flow channel into the second part during exhalation, and
         enable gas flow through the first flow channel from the second part during inhalation; and
      using a second valve of the second gas flow conveying element to:
         prevent gas flow through the second flow channel into lungs of the user during inhalation, and
         enable gas flow through the second flow channel into the first part during exhalation.

14. The method according to claim 13, comprising conducting exhaled gas through the second flow channel to the first part for increasing the pressure in the first part.

15. The device according to claim 13, comprising using a choke to induce flow resistance in the second flow channel.

16. The method according to claim 13, comprising:
limiting the gas flow in the first flow channel with the first valve when gas is flowing in the second flow channel, and
limiting the gas flow in the second flow channel with the second valve when gas is flowing in the first flow channel.

17. Use of the method of claim 13 for resistive exhalation and inhalation.

* * * * *